United States Patent [19]

Engel et al.

[11] 4,320,149

[45] Mar. 16, 1982

[54] USE OF FLUORINATED BETA-DIKETONES AS ANTIPLAQUE AGENTS

[75] Inventors: Michael R. Engel, White Bear Lake; Linda L. Aasen, Lakeland, both of Minn.

[73] Assignee: Minnesota Mining and Manufacturing Company, St. Paul, Minn.

[21] Appl. No.: 259,700

[22] Filed: May 1, 1981

Related U.S. Application Data

[63] Continuation-in-part of Ser. No. 84,989, Oct. 15, 1979, abandoned.

[51] Int. Cl.³ .................... A61K 31/12; A01N 35/00
[52] U.S. Cl. ....................................... 424/331; 424/49
[58] Field of Search ........................................ 424/331

[56] References Cited

U.S. PATENT DOCUMENTS 2,856,418 10/1958 Calvin .............................. 260/429.1
4,015,980 4/1977 MacKay et al. ...................... 75/120

FOREIGN PATENT DOCUMENTS 2088370 1/1972 France .
P72/24921 5/1972 South Africa .
1319247 6/1973 United Kingdom .

*Primary Examiner*—Allen J. Robinson
*Attorney, Agent, or Firm*—Cruzan Alexander; Donald M. Sell; Lorraine R. Sherman

[57] ABSTRACT

This invention relates to a process for inhibiting the formation of dental plaque in the oral cavity using certain fluorinated beta-diketones.

3 Claims, No Drawings

USE OF FLUORINATED BETA-DIKETONES AS ANTIPLAQUE AGENTS

This is a continuation-in-part of U.S. patent application Ser. No. 084,989, filed Oct. 15, 1979, now abandoned.

TECHNICAL FIELD

This invention relates to a process for inhibiting the growth of bacteria and particularly to inhibition of bacteria causing dental plaque.

BACKGROUND ART

There is a continual need for bactericidal materials and, in particular, it is desirable to have bactericides which inhibit *Streptococcus mutans* which is the principle cariogenic bacterium responsible for the formation of dental plaque. Dental plaque can give rise to caries, calculus, or inflammatory changes in adjacent tissue.

Beta-diketones are known particularly for their ability to chelate with various metals. It has been proposed to produce dental compositions containing complexes of 1,1,1-trifluoropentan-2,4-dione or 1,1,1,5,5,5-hexafluoropentan-2,4-dione with zinc, copper (II) or zirconium as described in British Patent Specification No. 1,319,247 and French Patent Application Ser. No. 2,088,370. These patents teach that mineralization of plaque into calculus can be inhibited using such compounds. Republic of South Africa Patent Application Ser. No. P 72/25921 teaches that zinc and copper complexes of certain betadiketones are useful in preventing tooth discoloration and tartar deposit. U.S. Pat. No. 4,015,980 teaches that zinc is extracted from aqueous ammoniacal solutions using certain $\beta$-diketones, and U.S. Pat. No. 2,856,418 discloses a process for separating plutonium from an aqueous solution of its tetravalent salt using certain fluorinated $\beta$-diketones.

DISCLOSURE OF INVENTION

In accordance with the present invention which provides a process for the control of the formation of dental plaque (i.e., control of bacteria known to form dental plaque in the oral cavity) it has been found that a growth inhibiting amount of certain beta-diketone compounds have useful antibacterial properties. In particular it is found that beta-diketone compounds represented by the general formula $$Y—CO—CH_2—CO—R_f \qquad I$$

wherein Y is an alkyl group having 4 to 20 carbon atoms, an alkenyl group having 4 to 20 carbon atoms, a halogen-substituted alkyl group having 4 to 20 carbon atoms, a halogen-substituted alkenyl group havng 4 to 20 carbon atoms, phenyl or naphthyl or their halogen-substituted derivatives, and $R_f$ is a perfluoroalkyl group containing one to three carbon atoms, inhibit the growth of *Streptococcus mutans* bacteria, precursors of dental plaque.

The use of some of these compounds as bacteriocides or fungicides is described in assignee's copending patent application, Ser. No. 259,702, filed the same date as this application.

DETAILED DESCRIPTION

The fluorinated beta-diketones useful in this invention is made by a simple synthesis method starting from the corresponding methyl ketone, $Y—CO—CH_3$, and condensing this with a fluorocarbon ester such as ethyltrifluoroacetate in the presence of a base. The reactants are dissolved in a polar solvent, such as ethanol, and refluxed for from several minutes to several hours. The resulting compounds, when solid, may be recrystallized or, when liquid, may be purified by distillation at reduced pressure.

To establish plaque control efficacy of the beta-diketones described in this invention, in vitro tests are performed on plaque-free bovine teeth. The teeth are dipped into a solution of the composition of the invention comprising 1% by weight fluorochemical in 99% by weight deionized water for 30 minutes. Untreated teeth serve as controls. The teeth and untreated teeth are suspended in tubes of a test medium comprising 18 milliliters of actinomyces broth, 2 milliliters of a 20% aqueous sucrose solution, and 0.2 milliliters of a 24 hour viable culture of *Streptococcus mutans*. The teeth and test tubes are incubated at 37° C. for 24 hours, after which the teeth are transferred to new test tubes of fresh test medium and again incubated at 37° C. for 24 hours. The procedure is repeated for three days or until attachment of plaque to the control teeth is noted.

Preferred compounds for use as anti-plaque agents in accordance with this invention are those wherein Y of formula I is an alkyl group of $C_5$ to $C_{12}$, the most preferred being the compound 1,1,1-trifluoropentadecandione-2,4.

Exempliary of beta-diketone compounds useful as dental anti-plaque agents are:

1,1,1,2,2-pentafluorodecanedione-3,5
1,1,1,2,2,3,3-heptafluoroundecanedione-4,6
1,1,1-trifluorononanedione-2,4
1,1,1-trifluoro-5-chlorononanedione-2,4
1,1,1-trifluorononene-5-dione-2,4
1,1,1-trifluoro-5-chlorononene-5-dione-2,4
1,1,1-trifluorodecanedione-2,4
1,1,1-trifluoropentadecanedione-2,4
1,1,1-trifluoroheptadecanedione-2,4
1,1,1-trifluorooctadecanedione-2,4
1,1,1-trifluoro-5-chlorooctadecanedione-2,4
1,1,1-trifluorooctadecene-5-dione-2,4
1,1,1-trifluoroheneicosanedione-2,4
1,1,1-trifluorotetracosanedione-2,4
1,1,1-trifluoro-4-phenylbutanedione-2,4
1,1,1-trifluoro-4-(4-chlorophenyl)butanedione-2,4
1,1,1-trifluoro-4-(1-naphthyl)butanedione-2,4
1,1,1,2,2-pentafluorooctanedione-3,5
1,1,1-trifluorooctanedione-2,4
1,1,1-trifluorooctenedione-2,4
1,1,1,2,2,3,3-heptafluorooctanedione-4,6

The compounds useful in this invention may be utilized in any preparations designed for application to the oral cavity which are referred to herein generally as dental compositions. Such dental compositions are suitable toothpastes and dental creams, tooth powders, mouthwashes, lozenges, tablets, chewing gum, dental floss or prophylactic gels. These compositions may contain as dental vehicles various adjuvant materials in suitable amounts provided the same do not substantially adversely affect the desired result.

Adjuvant materials include polishing agents, surface-active or detersive materials, water, glycerine or sorbitol, as well as additives such as water soluble saccharine, flavouring oils (e.g., oils of spearmint, peppermint, wintergreen), coloring or whitening agents (e.g., titanium dioxide), preservatives (e.g., sodium benzoate), emulsifying agents, alcohol, and menthol. Other suitable materials are chlorophyllin and various fluorides such as sodium monofluorophosphate, and stannous fluoride.

This invention is further illustrated by the following examples.

EXAMPLE 1

Compounds for use in the invention are prepared by condensation of lower alkyl trifluoroacetate, e.g. ethyl trifluoroacetate, with the appropriate alkanone using sodium alkoxide and subsequent acidification. This is illustrated by the following procedure.

A mixture of 11 g ethyltrifluoroacetate and 15 g methylundecylketone is gradually added over 15 minutes to a stirred solution of 2.0 g sodium metal in 75 ml ethanol in a 250 ml round bottomed flask. The mixture is refluxed for four hours and then allowed to stand overnight. The mixture solidifies and is decomposed by addition of 300 ml of 6 N hydrochloric acid. The oily organic phase is extracted with 150 ml ether, dried over anhydrous sodium sulfate, decanted, and the ether removed by evaporation. The resulting product, 1,1,1-trifluoropentadecandione-2,4 is a light yellow liquid distilled at 91° to 94° C. at 0.03 mm Hg. Yield is 12.5 gm.

A similar procedure using 2-octanone yields 1,1,1-trifluorodecandione-2,4 distilling at 40° to 42° C. at 0.1 mm Hg.

EXAMPLE 2

A mixture 29.6 g ethyltrifluoroacetate, 25.0 g acetophenone and 100 ml ether is added gradually with stirring over 10 minutes to a mixture of 100 ml ether and 17.5 g of a 57% sodium hydride dispersed in oil. The mixture is refluxed for three hours and stirred at room temperature for about 16 hours. The mixture is poured into 300 ml of hydrochloric acid. Ether is added and the ethereal phase separated, washed with a saturated sodium chloride solution and again separated and the ether evaporated. The resulting 1,1,1-trifluoro-4-phenylbutandione-2,4 is an oil distilling 55° C. at 0.1 mm Hg which crystallizes on standing.

EXAMPLE 3

The compounds of Table 1 are tested for control of plaque by the in vitro test described above.

TABLE 1

I. 1,1,1-trifluoro-heptandione 2,4 (outside scope of invention)

TABLE 1-continued

II. 1,1,1-trifluordecandione-2,4
III. 1,1,1-trifluoropentadecandione-2,4
IV. 1,1,1-trifluoro-4-phenylbutanedione-2,4

Duplicate tests are run parallel. Test data are recorded in Table 2 at daily intervals evaluated as follows:

| | |
|---|---|
| − − | no bacterial growth in entire tube |
| − | no bacterial growth on tooth and little bacterial growth in tube |
| 0 | no plaque growth on tooth but significant bacterial growth in tube |
| + | slight plaque growth on tooth |
| + + | plaque growth on tooth. |

TABLE 2

| Compound | Run | Day 1 | Day 2 | Day 3 | end |
|---|---|---|---|---|---|
| I | 1 | + + | + + | + + | + + |
| I | 2 | − | + + | + + | + + |
| II | 1 | − − | + | + + | + + |
| II | 2 | − − | − | + | + |
| III | 1 | − − | − − | − − | − |
| III | 2 | − − | 0 | 0 | − |
| IV | 1 | − − | − | + + | + |
| IV | 2 | − − | + | + + | + + |
| IV | 3 | 0 | + + | + + | + + |

It is evident from the above table that compound III is especially effective and that compound I which is outside the scope of the invention is essentially valueless.

What is claimed is:

1. The process of inhibiting the growth of *Streptococcus mutans* bacteria in the oral cavity which comprises providing in the environment of said bacteria a growth inhibiting amount of a beta-diketone compound represented by the formula

Y—CO—CH$_2$—CO—R$_f$ wherein Y is selected from the group consisting of an alkyl group having 4 to 20 carbon atoms, an alkenyl group having 4 to 20 carbon atoms, a halogen-substituted alkyl group having 4 to 20 carbon atoms, a halogen-substituted alkenyl group having 4 to 20 carbon atoms, phenyl or naphthyl and their halogen-substituted derivatives, and R$_f$ is a perfluoroalkyl group containing one to three carbon atoms.

2. A process in accordance with claim 1, wherein R$_f$ is CF$_3$.

3. A process in accordance with claim 2, wherein said beta-diketone is 1,1,1-trifluoropentadecandione-2,4.

* * * * *